United States Patent [19]

Bowsher et al.

[11] Patent Number: 4,649,107

[45] Date of Patent: Mar. 10, 1987

[54] PHENYLETHANOLAMINE N-METHYLTRANSFERASE BASED RADIOENZYMATIC ASSAY FOR NOREPHINEPHRINE

[75] Inventors: Ronald R. Bowsher, Beech Grove; David P. Henry, Indianapolis, both of Ind.

[73] Assignee: Eli Lilly and Company, Indianapolis, Ind.

[21] Appl. No.: 627,319

[22] Filed: Jul. 2, 1984

[51] Int. Cl.$^4$ .............................................. C12Q 1/48
[52] U.S. Cl. ...................................... 435/15; 435/193
[58] Field of Search ................................. 435/15, 193

[56] References Cited

U.S. PATENT DOCUMENTS 4,275,150  6/1981  Vlachakis ............................ 424/1.1
4,288,542  9/1981  Johnson et al. ........................ 435/15

OTHER PUBLICATIONS

Nagel-Hiemke et al., J. Biochem. Biophys. Meth. 4(1981), 255-9.
Molinoff et al., J. Pharmacol. Exp. Therapeutics, 178 (1971) 425-31.
Henry et al., "A Sensitive . . . Plasma", *Life Sciences* vol. 16, 375-384 (1975).
Lake et al., "Use of . . . Man", *Life Sciences* vol. 18, 1315-1326, (1976).
Falke et al., "Radioenzymatic . . . Extraction" *Clinica Chimica Acta*, 111-117 (1978).

*Primary Examiner*—Christine M. Nucker
*Attorney, Agent, or Firm*—Bruce J Barclay

[57] ABSTRACT

The present invention provides an improved method for quantifying endogenous norepinephrine employing a phenylethanolamine N-methyltransferase based radioenzymatic assay.

6 Claims, No Drawings

PHENYLETHANOLAMINE N-METHYLTRANSFERASE BASED RADIOENZYMATIC ASSAY FOR NOREPHINEPHRINE

BACKGROUND OF THE INVENTION

The mammalian sympathetic nervous system is composed of various cellular tissues having the unique capability of synthesizing postsynaptic neurotransmitter compounds. These compounds are biogenic amines termed catecholamines, a term derived from the catechol, or dihydroxybenzene, nucleus common to each of the compounds. These catecholamines include dopamine, norepinephrine and epinephrine.

Aberrations of the sympathetic nervous system can lead to a wide variety of adverse clinical manifestations. Therefore, accurate and reliable methods for quantifying the concentration of catecholamines in the body are critical to provide adequate monitoring of the system. Further, since these compounds are present in the body in very small amounts, the methods must be highly sensitive, that is, capable of detecting the compounds in very small amounts. The frequency at which these methods are conducted mandate further that they be highly reproducible under laboratory conditions when employing a variety of body tissues and fluids and provide the results quickly in order to facilitate diagnosis.

Radioenzymatic assays are sensitive analytical methods which have found wide use in the quantification of various biogenic amines. These assays are based on the enzymatic methylation of a specified compound to a radiolabeled product by an appropriate enzyme employing radioactive S-adenosylmethionine as the methyl donor. Most of the currently employed radioenzymatic assays lack the sensitivity necessary to quantify catecholamines in important biological samples such as human plasma.

Henry et al. in *Life Sciences* 16:375 (1975) describe a useful radioenzymatic assay for specifically measuring norepinephrine in tissues, plasma and urine. This method relates to the conversion of norepinephrine to radiolabeled epinephrine employing partially purified bovine adrenal phenylethanolamine N-methyltransferase and tritiated S-adenosylmethionine.

The present invention relates to an improved radioenzymatic assay for norepinephrine comprising the methylation of norepinephrine with purified phenylethanolamine N-methyltransferase to radiolabeled epinephrine employing tritiated S-adenosylmethionine as the methyl donor. The tritiated epinephrine thus obtained may then be conveniently isolated by batch alumina chromatography and any residual unreacted tritiated S-adenosylmethionine may be removed by precipitation upon treatment with phosphotungstic acid. Further, the tritiated epinephrine may be quantified by liquid scintillation spectrometry using a biphasic counting system which employs an ion-pair reagent containing bis(2-ethylhexyl)hydrogen phosphate to extract the tritiated epinephrine into a high efficiency counting environment.

SUMMARY OF THE INVENTION

The present invention relates to a method for quantifying norepinephrine comprising the following steps:

A. incubating a mixture comprising an appropriate norepinephrine containing sample, substantially purified phenylethanolamine N-methyltransferase, [$H^3$]S-adenosylmethionine and a suitable buffer at a temperature in the range of about 20° C. to about 45° C. for a period of about 10 to 60 minutes;

B. terminating the reaction by the addition of a potassium phosphate buffer containing a reducing agent to the mixture in (A);

C. adding alumina to the mixture in (B) to provide an alumina-tritiated epinephrine complex;

D. washing the alumina-tritiated epinephrine complex in (C) with water and separating the alumina from the tritiated epinephrine by elution with a suitable acid solution;

E. adding phosphotungstic acid to the solution in (D) containing tritiated epinephrine;

F. combining the supernatant in (E) with a phosphate buffer, bis(2-ethylhexyl)hydrogen phosphate and a counting scintillator; and G. counting the radiation emitted from the tritiated epinephrine contained in the mixture in (F).

DETAILED DESCRIPTION OF THE INVENTION

There are two general classes of norepinephrine radioenzymatic assays depending on the type of methyltransferase enzyme employed in the radiolabeling reaction. This methyltransferase enzyme can be either catechol O-methyltransferase or phenylethanolamine N-methyltransferase.

Catechol O-methyltransferase methylates each of the three endogenous catecholamines listed above, as well as another catechol containing compound, and therefore can be employed to measure each of these compounds in biologic samples. However, the methylated product of each of the catecholamines must be separated, and typically this procedure has been accomplished by rather laborious and time consuming thin layer chromatography separations. In contrast, phenylethanolamine N-methyltransferase will only methylate norepinephrine, thereby affording specificity in the quantification of this biogenic amine. Other endogenous non-catechol containing substrates for phenylethanolamine N-methyltransferase do exist but the methylated products of these compounds do not adsorb to alumina which is specific to catechols.

The biochemical principle of the present norepinephrine assay is illustrated by the following reaction scheme:

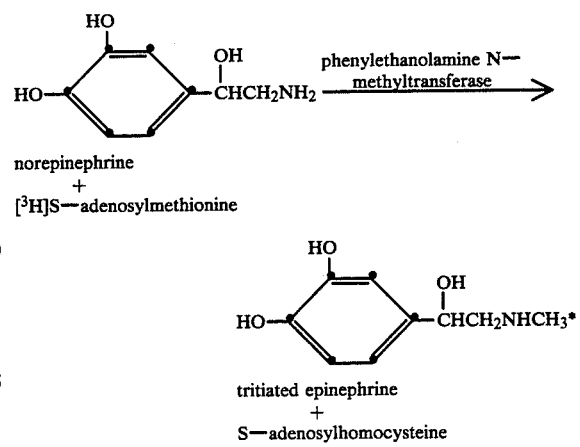

The present phenylethanolamine N-methyltransferase based norepinephrine radioenzymatic assay is typically conducted by preparing reference standards for comparative purposes. Typically the assay is conducted in duplicate and an average cpm value calculated for each of the standards.

The incubate employed in the present assay comprises an enzyme solution and sufficient quantity of an appropriate norepinephrine containing sample to be tested. The enzyme solution is typically prepared by combining a suitable buffer with ascorbic acid, substantially purified phenylethanolamine N-methyltransferase and tritiated S-adenosylmethionine.

Appropriate norepinephrine containing samples are employed in the present assay in an effort to quantify the concentration of norepinephrine contained therein. While any material containing norepinephrine may be employed in the assay, the preferred sample is a mammalian tissue extract. Exemplary extracts of this type include human plasma, urine and tissue. One advantage of the increased sensitivity of the present assay is the need for minimal sample preparation as compared to existing radioenzymatic assays. Due to the improved stability of catechols in mildly acidic conditions, acids having minimal buffer capacity are preferably added to the incubate. Suitable acids include those capable of forming a pH in the range of about 3 to 4 and include mineral acids such as hydrochloric acid and acetic acid.

Suitable buffers for use herein include those having a pH in the range of about 8 to 9. Exemplary buffers of this type include tris, bis-tris propane, tes, HEPES and the like. It is also preferred to have a chelating agent such as ethylenediaminetetraacetic acid (EDTA) present in the buffer solution.

Tritiated S-adenosylmethionine is the labeled methyl donor employed in the present enzymatic methylation. This tritium labeled methyl donor can be made by radiochemical methods known in the art and is commercially available from New England Nuclear Corp., Boston, Mass. and Amersham Corp., DesPlains, Ill. The tritium label is at the methyl group adjacent to the sulfonium ion. It has now been found that this methyl donor should be present in the incubation mixture at a concentration $\geq$ about 0.1 $\mu$M for maximal activity. In order to produce the excellent sensitivity of this assay, the labeled methyl donor is preferably essentially free of unlabeled, cold methyl donor S-adenosylmethionines. The addition of unlabeled, cold methyl donor makes the assay less sensitive for norepinephrine. If a less sensitive assay is desired, this may be achieved by adding unlabeled, cold S-adenosylmethionine to the assay incubate. The tritium labeled [$H^3$]S-adenosylmethionine should be prepared with maximum specific activity for optimal sensitivity of the assay. While generally radioactivity greater than or equal to about 8 Ci/mmol can be employed, preferred radioactivity will be from about 60 to about 85 Ci/mmol.

The term "substantially purified phenylethanolamine N-methyltransferase", as used herein, is defined as enzyme having a composition essentially free from foreign contaminants and of sufficient purity so as to be suitable for use in radioenzymatic assays. It has been determined experimentally that the purity of enzyme used in the present radioenzymatic assay is critical in affording adequate sensitivity and specificity to the assay.

The following procedure illustrates the method for obtaining substantially purified phenylethanolamine N-methyltransferase suitable for use in the present norepinephrine assay. This procedure is designed to remove competing methyltransferase enzymes and naturally occuring catecholamines.

In mammals, it has been determined that this enzyme is localized almost exclusively in the adrenal gland with trace amounts also present in the heart and brain. Thus, while the adrenal medulla represents the preferred tissue source for the isolation of phenylethanolamine N-methyltransferase, due to size limitations of adrenals of most species the only practical source of the enzyme is bovine glands.

Once isolated, the enzyme containing mammalian tissue is immediately chilled, for example by submersion in an isotonic solution of sodium chloride. When used, the temperature of this solution is maintained in the range of about 0° C. to about 5° C. This temperature range is also employed for all subsequent steps of the enzyme purification method as well. Typically, once in the laboratory, any fat or cortical tissue is removed from around the mammalian tissue to provide only enzyme containing mammalian tissue. When using adrenal glands, the adrenal cortex is also removed due to its high lipid content which hinders subsequent enzyme purification.

The mammalian tissue thus isolated must be disrupted in order to facilitate extraction of the enzyme. Tissue disruption may be conducted mechanically by any of several well known procedures such as sonication, by means of a tissue press or preferably by homogenization. Homogenization may be conducted by any one of several routine procedures but is preferably carried out by first mincing the enzyme containing tissue into small pieces and then combining these pieces with an isotonic media in an homogenizer. Homogenizers suitable for use herein include blenders and other instruments, such as a Brinkmann Polytron. Suitable isotonic media include potassium chloride or a phosphate buffer. The preferred isotonic media is an isotonic sucrose solution. While the amount of isotonic media employed should be sufficient to completely solubilize the enzyme, the isotonic media is preferably employed at a volume of approximately 3 to 10 times the volume of the mammalian tissue sample.

The tissue suspension is then centrifuged for a period of about 15 to 60 minutes at a force in the range of about 10000 x g to about 60000 x g. Centrifugation is preferably conducted for about 15 minutes at a force of about 40000 x g. The supernatant thus formed is then filtered, typically through gauze, so as to remove the lipid layer. The filtered supernatant is then typically centrifuged at a force of about 100,000 x g to 300,000 x g for a period of about 15 to about 120 minutes so as to remove storage granules known to contain high levels of norepinephrine and epinephrine. Centrifugation is preferably conducted at a force of about 220,000 x g for a period of approximately 90 minutes.

The supernatant thus prepared is isolated and slurried with solid enzyme-grade ammonium sulfate which causes the enzyme to precipitate. The purpose of the ammonium sulfate precipitation is to remove any soluble norepinephrine or epinephrine and to simultaneously concentrate the enzyme preparation. The ammonium sulfate is employed at a concentration in the range of about 55% to about 85%, more preferably at a concentration to provide about a 65% saturated solution of ammonium sulfate (413 g of ammonium sulfate for each 1000 ml of enzyme preparation). The preparation is stirred for a period of about 5 to about 60 minutes, preferably for about 20 minutes, and centrifuged at about 40000 x g for about 10 minutes.

The supernatant is discarded and the precipitate is suspended with a suitable buffer having a pH in the range of about 7.0 to 9.0. Suitable buffers for use in this purification method will have a pH in the range of about 7.0 to about 9.0 and should be cation buffers such as tris, bis-tris and bis-tris propane. These buffers are known in the biochemical art and commercially available. The preferred buffer employed in the suspension of the precipitate is a solution of tris(hydroxymethyl)aminomethane and a chelating agent such as ethylenediaminetetraacetic acid (EDTA).

The pH of the enzyme preparation is adjusted to approximately 4.5 to 5.5 by the slow addition of an appropriate weak acid, which is any acid capable of forming a buffer in this pH range. The preferred weak acid employed herein is cold acetic acid. This mixture is then centrifuged and the supernatant is decanted and transferred to dialysis bags.

The supernatant is dialyzed for approximately 24 hours against a sodium acetate solution at pH of approximately 4.5 to 5.5. Typically one buffer change is required although more may be employed as needed. It should also be noted that during the dialysis process additional protein will typically precipitate. The dialyzed preparation is then centrifuged and the supernatant is decanted. The precipitate is discarded. The supernatant is titrated to a pH of approximately 7.0 to 7.5 upon the slow addition of a base such as ammonium hydroxide and adjusted to a concentration of approximately 1 mM by the addition of dipotassium EDTA.

The dialysis procedure described above has two functions. First, dialysis at an acidic pH efficiently removes endogenous norepinephrine and epinephrine. Secondly, substantial enzyme purification is achieved since phenylethanolamine N-methyltransferase is very stable at a pH around 5, while approximately two-thirds of the other total proteins are removed at this step. Further, it is believed that pH 5 treatment is an efficient process for removing endogenous thiol S-methyltransferase, a known inhibitor of enzyme activity.

The enzyme preparation described above is concentrated by precipitation with ammonium sulfate fractionation at about 55% to about 85% saturation. This preparation is typically about 65% saturated. The precipitate is collected and centrifuged and the supernatant is suspended in a suitable buffer-EDTA system as described above at a pH of approximately 8.

The enzyme buffer solution is next desalted by dialysis or by molecular exclusion chromatography which is capable of separating molecules by molecular weight. This chromatography material is readily available. The preferred material is Ultrogel ACA 202 commercially available from LKB Corp., Gaithersburg, Md. As the fractions elute from the column they are typically assayed to localize phenylethanolamine N-methyltransferase activity by any one of several routine methods such as UV spectrometry, enzyme assays and the like.

Molecular size exclusion chromatography has two functions. First, the column has the ability to retain those molecules having a molecular weight of approximately 22,000 or less thereby effectively removing small molecules such as norepinephrine and epinephrine. Secondly, the column removes any salts and therefore facilitates subsequent anion-exchange chromatography.

The enzyme preparation is next applied to an anion-exchange chromatography column. Anion-exchange chromatography includes the use of a column material comprised of an alkylamine, for example a diethylaminoethyl or triethylaminoethyl moiety, covalently attached to any of a variety of matrices such as cellulose or any of a number of other polymers. A variety of these chromatographic materials are commercially available and the preferred material is sold by Pharmacia Chemicals as diethylaminoethyl-Sephacel. The column is previously equilibrated with a suitable buffer having a pH of approximately 8. The column is eluted with the same buffer until all non-adsorbed protein has been eluted. The enzyme activity is then eluted preferably with the same buffer containing sodium chloride, and the enzyme containing fractions are collected and concentrated by routine methods, such as by ultrafiltration.

Anion-exchange chromatography has two functions. First, cations such as norepinephrine and epinephrine will not bind to the column. Thus the column helps remove these interfering substances. Secondly, this column removes uncharacterized inhibitors of the enzyme reaction.

The concentrated enzyme preparation is next further purified with molecular size exclusion chromatography. The column is typically equilibrated with a buffer having a pH in the range of about 7.5 to 8.5 prior to the enzyme purification. The column is eluted with buffer and the fractions containing the enzyme are combined. Molecular size exclusion effectively removes smaller molecules capable of reducing the purity of the enzyme preparation.

The combined fractions containing the isolated enzyme are applied to a boronate-agarose chromatography column previously equilibrated with a potassium buffer at approximately pH 7.5 to 9.5, such as potassium HEPES. Boronate-agarose columns contain an agarose gel with bound borate. This material is capable of complexing cis-diols, such as catecholamines, and is thereby capable of further purifying the enzyme preparation by removing endogenous catecholamines. This material is commercially available in a variety of forms. The preferred material is PBA-60, a phenylboronate-agarose column commercially available from Amicon. As the column is eluted with the buffer, the nonabsorbed protein is typically collected as a single fraction. The collected enzyme solution is concentrated and suitable for use in the present norepinephrine radioenzymatic assay. The boronate-agarose column has a very high capacity for catecholamines and as such this column is extremely valuable in the removal of residual norepinephrine and epinephrine. This procedure is taught in Ser. No. 627,320, filed July 2, 1984, filed even date herewith.

All the quantities of the incubate are present in amounts which allow the norepinephrine concentration of the mammalian tissue sample to be the rate limiting factor. The enzyme solution is present in quantities in excess of those quantities necessary to bring about the timely conversion of norepinephrine to tritiated epinephrine. All, or essentially all, of the norepinephrine present in the mammalian tissue sample to be assayed is converted to tritiated epinephrine during the incubation period.

The enzymatic incubation is carried out in standard laboratory equipment for a time and at a pH and temperature which allows the enzymatic conversion to go to completion. The pH of the incubate should be maintained between about 7 and about 10. The preferred pH range is from about 8 to about 9. Typically, the assay tubes containing the incubate are incubated gently for a period of about 10 to 60 minutes at a temperature in the range of about 20° C. to about 45° C. Preferably the tubes are incubated for about 30 minutes at about 37° C.

The methylation reaction of norepinephrine to epinephrine is terminated by the addition of a buffer solution containing potassium phosphate and EDTA as well as a reducing agent such as dithioerythritol, ascorbic acid, mercaptoethanol or especially dithiothreitol. The mixture is then agitated.

The next step of the present assay involves batch alumina adsorption chromatography. In this step a sufficient amount of alumina is added to the mixture in order to adsorb tritiated epinephrine.

The specificity of the batch alumina adsorption chromatography employed herein has been optimized by controlling the pH, phosphate concentration and volume of adsorption buffer relative to the mass of alumina. It has been determined that these factors are critical in reducing the nonspecific adsorption of tritiated S-adenosylmethionine and other materials by alumina. Generally it is preferred to employ a high concentration potassium phosphate buffer, for example in the range of about 0.5M to about 1.5M concentration, with a smaller volume of liquid in order to facilitate the binding of catechols to alumina. While the ratio of the volume of liquid to the volume of alumina employed in this step may vary, preferably approximately an equivolume amount of liquid and alumina will be employed.

The supernatant is separated from the solid alumina-tritiated epinephrine complex prepared above and discarded. This complex is washed with water and the tritiated epinephrine is separated from the alumina upon elution with a cold suitable acid solution. Suitable acids include any strong acid such as hydrochloric, nitric and especially perchloric acid. The acid solution is prepared by dissolving unlabeled S-adenosylmethionine in a dilute acid solution containing an excess of epinephrine. Each of the tubes is then vortexed and any residual labeled or unlabeled S-adenosylmethionine is precipitated upon the addition of a solution of aqueous phosphotungstic acid. Blank reduction is afforded by precipitation of unreacted tritiated S-adenosylmethionine with phosphotungstic acid to provide an acid complex. Each of the tubes is then vortexed and centrifuged in order to remove the alumina.

The next step of the present radioenzymatic assay involves the quantification of the tritiated epinephrine. While not disturbing the S-adenosylmethionine precipitate, the epinephrine containing supernatant is removed and transferred to a scintillation vial containing a phosphate buffer. Suitable phosphate buffers include sodium, lithium and especially potassium phosphate. Next a counting solution is added to each vial. This counting solution is prepared by combining bis(2-ethylhexyl)hydrogen phosphate (DEHP) with a counting scintillator. The scintillator is also typically solubilized with an organic solvent such as toluene. The particular counting scintillator employed is not significant as long as it will emit a quantum of light when exposed to a β-ray emitted from tritium. Examples of suitable scintillators are p-terphenyl; 2,5-diphenyloxazole; 2-phenyl-5-(4-biphenylyl)-1,3,4-oxadiazole, 2,5-bis-2-(5-t-butylbenzoxazolyl)thiophene; 2,5-diphenyl-1,3,4-oxadiazole; 2-(4'-biphenyl)-6-phenylbenzoxazole; 1,4-bis-2-(5-phenyloxazolyl)benzene. Counting scintillators are commercially available under a variety of names such as Liquifluor, from New England Nuclear or OCS, an organic counting scintillant from Amerscham. The vials are capped and shaken. The radiation emitted by the tritiated epinephrine is counted by devices typically employed in liquid scintillation spectrometry.

The tritiated epinephrine formed is extracted by the DEHP/organic solvent mixture, a cation specific ion-pair reagent. The DEHP/organic solvent extraction results in an unquenched scintillation sample with no significant additional costs or manipulative effort and substantial blank reduction.

After counting the radiation emitted by the tritiated epinephrine, the concentration of norepinephrine in each mammalian tissue sample is calculated according to the following formula:

$$\text{Norepinephrine Concentration (pg/ml)} = \frac{\text{Sample cpm} - \text{Blank cpm}}{(\text{Sample} + \text{Standard}) \text{ cpm} - \text{Sample cpm}} \times \frac{\text{Standard pg}}{\text{Sample Volume ml}}$$

As used herein, the term "sample" represents an incubate prepared as described herein containing an appropriate norepinephrine containing sample to be assayed. The incubate is assayed as described herein and a counts per minute (cpm) value is obtained.

The term "blank", as used herein, represents an incubate containing all of the ingredients except the norepinephrine containing sample. This mixture is assayed in the manner described herein and a cpm value is obtained.

The term "standard", as used herein, represents an incubate containing the same components as described herein except the incubate includes a specific quantity of exogenous norepinephrine in addition to the norepinephrine containing sample. Again this mixture is assayed by the same procedure as described herein and a cpm value is obtained.

The present norepinephrine radioenzymatic assay exhibits several unique properties. First, the assay has been shown to be highly sensitive, that is, capable of detecting amounts of norepinephrine in quantities of less than one picogram. The assay also has very high specificity and the intraassay coefficient variation is less than 5%. Secondly, the results of the assay may now be more quickly ascertained when employing the present radioenzymatic assay. Since no thin layer chromatography separations are required in the present assay, manipulative effort is minimized and accordingly a higher sample throughput may be obtained. For example, a 60 tube assay may be routinely completed within 3 hours when employing the present assay technique. Finally, the equipment required to conduct the present assay is commonly employed in any typical biomedical laboratory. Exotic or expensive equipment is not necessary to conduct the present radioenzymatic assay. In view of the advantages described above the present radioenzymatic assay of norepinephrine could be conveniently contained in a diagnostic kit commercially available for use by physicians and biomedical laboratory personnel. Only a minimal amount of preparation would be required by the operator before conducting the present assay.

In summary, specificity of the present improved norepinephrine radioenzymatic assay is afforded by the specificity of the phenylethanolamine N-methyltransferase radiolabeling reaction, the specificity of alumina for catecholamines and the selectivity of DEHP for cations. Blank reduction is provided by phosphate buffered batch alumina chromatography, phosphotungstic acid precipitation of unreacted tritiated S-adenosylmethionine and DEHP ion-pair solvent extraction.

The following example illustrates the use of the present norepinephrine radioenzymatic assay. The example is not intended to be limiting to the scope of the present invention in any respect and should not be so construed.

Quantification of Norepinephrine using Phenylethanolamine N-Methyltransferase

The following norepinephrine radioenzymatic assay was performed in 12 mm×75 mm disposable borosilicate culture tubes. All assays were conducted in duplicate.

Four sets of two culture tubes were prepared for use in the present assay as follows. The first set of tubes was blank tubes each containing 50 μl of 0.001M hydrochloric acid. The second set of tubes was sample tubes containing 25 μl of 0.001M hydrochloric acid and 25 μl of plasma. The third set of tubes was internal standard tubes containing 25 μl of 0.001M hydrochloric acid, containing 500 pg of norepinephrine and 25 μl of plasma. The fourth and final set of tubes was external standard tubes containing 25 μl of 0.001M hydrochloric acid and 25 μl of 0.001M hydrochloric acid containing 500 pg of norepinephrine.

To initiate the reaction 25 μl of a freshly prepared reaction mixture was added to each tube as described above to provide a final reaction volume of 75 μl. This reaction mixture was prepared as follows. Two hundred microliters of a solution containing 1M Trizma hydrochloride (tris(hydroxymethyl)aminomethane hydrochloride available from Sigma Chemical Company, St. Louis, Mo.) and 2 g per 100 ml of EDTA at pH 8.6 were combined with approximately 2.5 mg of ascorbic acid, 250 μl of distilled water, 50 μl of purified phenylethanolamine N-methyltransferase and 50 μl of tritiated S-adenosylmethionine (commercially available from Amersham).

The assay tubes thus prepared were vortexed gently and incubated for 30 minutes at 37° C. in a water bath. The reaction was terminated by the addition of 100 μl of a solution containing 2M potassium phosphate and EDTA at a concentration of 2 g for each 100 ml at pH 10 and also containing approximately 1 mM of dithiothreitol. Each of the tubes was vortexed and then charged with 50 mg of alumina. Each of the tubes was vortexed again and centrifuged for 5 minutes at approximately 2500 x g. The supernatant was aspirated by vacuum and the resulting alumina was washed three times by vortexing following the addition of about 1 to 2 ml of distilled water. After each wash the alumina was allowed to settle by gravity and the water was removed by aspiration. After the third wash and aspiration the tritiated epinephrine was eluted from the alumina upon the addition of a cold perchloric acid solution. This solution was prepared by dissolving 2.5 mg of unlabeled S-adenosylmethionine in approximately 20 ml of cold 0.1 M perchloric acid containing approximately 0.5 mg epinephrine. Each assay tube was vortexed for approximately 1 to 3 seconds following addition of 1 ml of this solution. Any residual tritiated or unlabeled S-adenosylmethionine was precipitated by the addition of 200 μl of a freshly prepared phosphotungstic acid solution. This solution was prepared by combining 0.5 g of phosphotungstic acid with 4 ml of deionized water. After vortexing each of the tubes the precipitate and alumina were precipitated by centrifugation for 5 minutes at 2500 x g.

The following process was used to quantify the tritiated epinephrine.

While not disturbing the S-adenosylmethionine precipitate a 1 ml aliquot of supernatant from each culture tube was directly transferred to individual scintillation vials each containing 1 ml of a 1M potassium phosphate solution at pH 7.1. The 1M potassium phosphate solution was prepared by combining 136.1 g of potassium phosphate with a sufficient quantity of water to bring the total volume of the solution to one liter. The pH was adjusted to 7.1 with 10M potassium hydroxide and the solution was stored in the refrigerator at approximately 10° C. to retard microbial growth. Next, 10 ml of a counting solution was added to each vial. This solution was prepared by combining 80 ml of bis(2-ethylhexyl)-hydrogen phosphate (Eastman) with 4 liters of OCS or Econofluor. The vials were capped, shaken and quantified by liquid scintillation spectrometry as a biphasic system.

We claim:

1. A method for quantifying norepinephrine comprising the following steps:
   A. incubating a mixture comprising an appropriate norepinephrine containing sample, substantially purified phenylethanolamine N-methyltransferase essentially free from foreign contaminants including thio S-methyltransferase and of sufficient purity so as to be suitable for use in radioenzymatic assays, S-adenosylmethionine and a suitable buffer at a temperature in the range of about 20° C. to about 45° C. for a period of about 10 to 60 minutes;
   B. terminating the reaction by the addition of a potassium phosphate buffer containing a reducing agent to the mixture in (A);
   C. adding alumina to the mixture in (B) to provide an alumina-tritiated epinephrine complex;
   D. washing the alumina-tritiated epinephrine complex in (C) with water and separating the alumina from the tritiated epinephrine by elution with a suitable acid solution;
   E. adding phosphotungstic acid to the solution in (D) containing tritiated epinephrine;
   F. combining the supernatant in (E) with a phosphate buffer, bis(2-ethylhexyl)hydrogen phosphate and a counting scintillator; and
   G. counting the radiation emitted from the tritiated epinephrine contained in the mixture in (F).

2. A method of claim 1 wherein the appropriate norepinephrine containing sample is human plasma.

3. A method of claim 1 wherein the appropriate norepinephrine containing sample is urine.

4. A method of claim 1 wherein the suitable buffer is tris.

5. A method of claim 1 wherein the reducing agent is dithiothreitol.

6. A method of claim 1 wherein the suitable acid is perchloric acid.

* * * * *